United States Patent [19]

Gogol, Jr. et al.

[11] 4,381,894
[45] May 3, 1983

[54] DEPOSITION MONITOR AND CONTROL SYSTEM

[75] Inventors: Carl A. Gogol, Jr., Cazenovia; Eric T. Prince, Fayetteville, both of N.Y.

[73] Assignee: Inficon Leybold-Heraeus, Inc., East Syracuse, N.Y.

[21] Appl. No.: 204,644

[22] Filed: Nov. 6, 1980

[51] Int. Cl.³ .................... G01N 21/84; G01N 21/31
[52] U.S. Cl. ................................. 356/72; 356/320; 356/407; 118/712
[58] Field of Search ............... 356/72, 73, 320, 407; 118/712

[56] References Cited

U.S. PATENT DOCUMENTS

| | | | |
|---|---|---|---|
| 3,694,086 | 9/1972 | May | 356/320 |
| 3,734,620 | 5/1973 | Cade | 356/73 |
| 3,817,622 | 6/1974 | Billman et al. | 356/73 |
| 3,895,233 | 7/1975 | Boll et al. | 356/437 |
| 4,247,205 | 1/1981 | Typpo | 356/407 |

OTHER PUBLICATIONS

"A Dualwave-Length Atomic Absorption Spectrometer for the Determination of Lead in Blood." Dawson et al., 17th International Spectroscopy Colloquim, vol. 1, Florence Italy (Sep. 16-22, 1973) pp. 231-234.
"A High-Performance Dual-Wavelength Spectrophotometer and Fluorometer," Schmidt, J. of Biochemical and Biophysical Methods, 2(1980) 171-181.

Primary Examiner—Vincent P. McGraw
Attorney, Agent, or Firm—Bruns & Jenney

[57] ABSTRACT

Method and apparatus for monitoring the deposition of a material or materials upon a substrate using atomic absorption techniques. Radiant energy is directed through a flow of evaporant during a deposition process. The radiation contains spectral emission lines absorbable by the evaporant as well as emission lines not absorbable by the evaporant. Changes in the transmission of one or more non-absorbable lines are used to compensate for changes in the absorption of absorbable lines of interest that are caused by misalignment or displacement of the optical elements during the deposition process.

8 Claims, 3 Drawing Figures

DEPOSITION MONITOR AND CONTROL SYSTEM

BACKGROUND OF THE INVENTION

This invention relates to atomic absorption spectroscopy and, in particular, to an improved technique for monitoring and controlling the rate of deposition of a material upon a substrate.

As disclosed in U.S. Pat. Nos. 3,734,620 and 3,654,109, prior art deposition monitor and control systems have been developed which utilize atomic absorption spectroscopy principles. In these systems, selected spectral emission lines absorbable by an evaporant are directed through an evaporant flow. The atomic absorption of the flow material is deduced from the ratio of the transmission of one or more absorbable lines through the evaporant to the transmission of the line or lines through the same vapor free path. Although absorption relates technically to the number density of the evaporant atoms in the optical path of the system, it can be correlated to the rate of deposition of the evaporant upon a specific substrate as explained in the noted patents. Accordingly, if all other system parameters are held constant, each of the transmission measurements can be considered essentially a function of the number density and the correlated rate thus used as a valid indication of the actual deposition rate.

It has been found, however, that not all system parameters remain constant during the deposition process. The alignment of the optical elements, which are typically attached to the vacuum chamber, oftentimes changes during the deposition process due to thermal expansion of the chamber. Misalignment or displacement of the optical elements has been shown to cause changes in observed absorption as high as 15% of the total absorption measurement. Atomic absorption deposition monitoring systems heretofore have been unable to separate changes in transmission due to changes in evaporant density (deposition rate) from those due to misalignment of the optics. Consequently, under certain conditions, the transmission measurements required for precise deposition monitoring and control cannot be acquired without interrupting the process so that new zero absorption readings can be taken. Interrupting a deposition run prior to its completion is generally not practical.

SUMMARY OF THE INVENTION

It is therefore an object of the present invention to improve systems for monitoring and controlling the deposition rate of an evaporant.

A further object of the present invention is to correct absorption measurements taken by an atomic absorption monitor for changes that are not related to changes in the number density of the evaporant atoms.

A still further object of the present invention is to separate changes in transmission that are caused by changes in the number density of evaporant atoms from those changes caused by the misalignment of the optical measuring elements during a deposition run.

Yet another object of the present invention is to continually correct for changes in the transmission of the optical system of an atomic absorption deposition monitor and control system while the evaporant flow is in process and correcting absorption measurements in response to changes therein.

Yet a still further object of the present invention is to improve the calibration of an atomic absorption deposition monitor and control system over extended periods of time.

These and other objects of the present invention are attained by method and apparatus using atomic absorption spectroscopy principles and techniques to both accurately monitor and control the rate at which an evaporant is deposited upon a specific substrate. The apparatus includes a source of radiation (light) that is directed through an established flow of evaporant as it is being deposited upon the substrate. The radiation contains emission lines absorbable by the evaporant along with emission lines not absorbable by the evaporant. Measured changes in the transmission of one or more non-absorbable lines, which are not related to changes in the number density, are used to correct absorption and/or transmission measurements obtained using one or more absorbable emission lines. In one embodiment of the invention, changes in the observed deposition rate are utilized to provide control signals for regulating the deposition equipment.

BRIEF DESCRIPTION OF THE DRAWINGS

For a better understanding of these and other objects of the present invention, reference is made to the following detailed description of the invention which is to be read in conjunction with the accompanying drawings, wherein.

DESCRIPTION OF THE INVENTION

Figure 1:
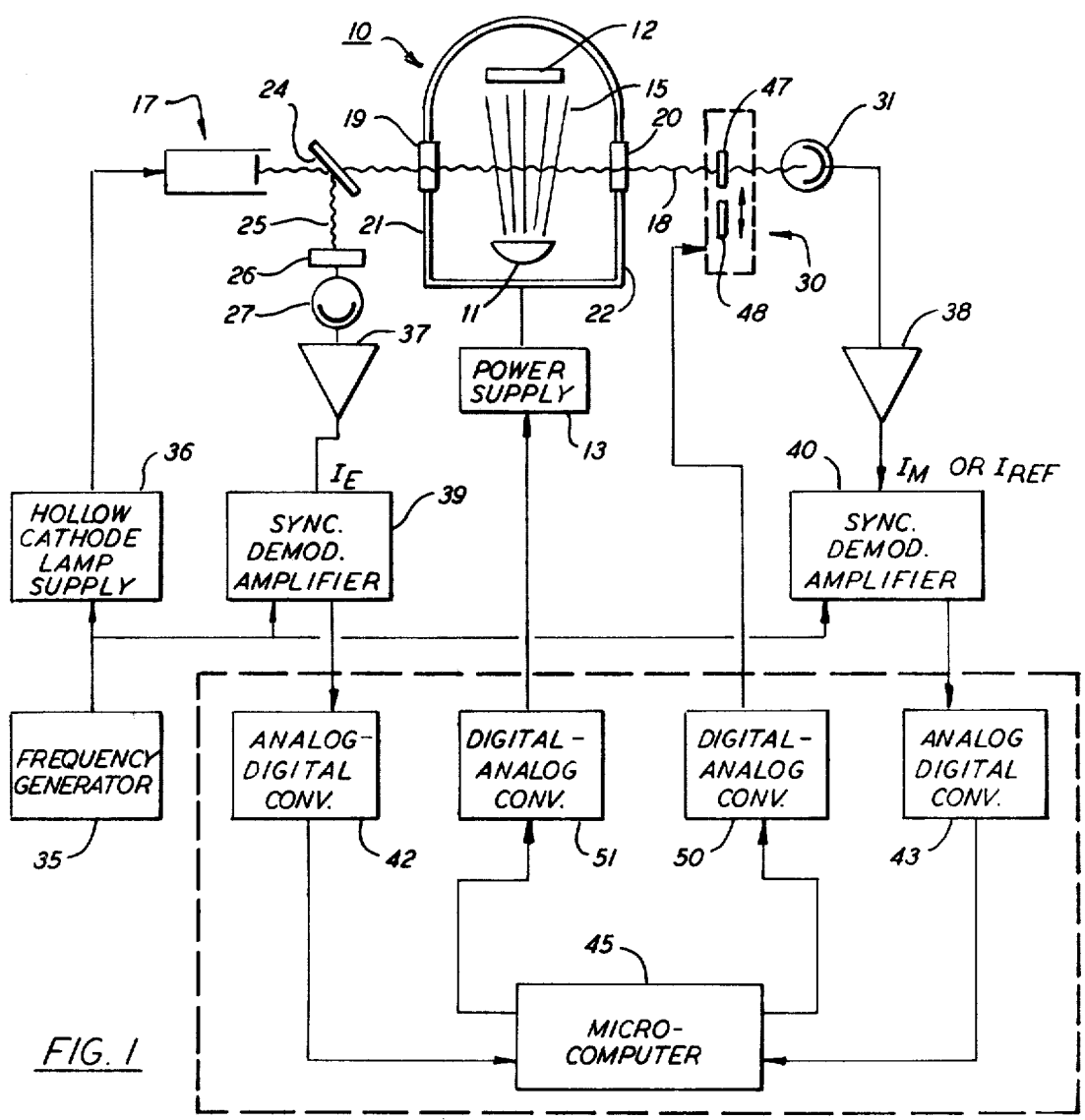
FIG. 1 is a schematic diagram illustrating a vacuum deposition monitor/control system embodying the teaching of the present invention.

With reference to the drawings, an atomic absorption deposition monitor and control system will be herein described that has the ability to measure the eqivalent transmission of the optical system at zero absorption while the process is in progress and, in response to changes therein, correct evaporant flow related transmission and/or absorption measurements that are used to both monitor and control evaporant flow rates. Since these zero absorption transmission measurements are taken while the deposition process is in progress, the system overcomes a significant and long standing problem associated with similar prior art devices. In the practice of the present invention, a source of radiation (light) is provided in the form of a Hollow Cathode lamp that is capable of producing emission lines over a relatively wide spectal range. The cathode is composed at least in part of the evaporant material while the fill gas is formed of a material or materials not related to the evaporant. The lamp thus produces emission lines that are characteristic of the evaporant material, and thus absorbable by the evaporant, and lines that are characteristic of the fill gas which, in turn, are not absorbable by the evaporant.

Radiation from the lamp is passed through a well established or defined path of the evaporant between the source and a substrate that is being coated. Two individual sets of transmission readings are taken. The first set of measurements concern a first selected wavelength region that includes one or more emission lines which are absorbable by the evaporant of interest. The second set of measurements concern a second selected wavelength region that includes one or more emission lines that are not absorbable by the subject evaporant. The subject wavelength regions shall be herein referred to generally by the terms first and second wavelengths with the understanding that the term wavelength defines a region of wavelengths containing one or more successive emission lines of the same material. The measured transmission of the first wavelength is a function of two variables. One variable involves the deposition rate, or more precisely the number density of the evaporant atoms in the observed flow, and the other variable involves relative movement of the optical elements utilized in the system. The measured transmission of the second wavelength is not affected by the evaporant flow and is solely a function of optical alignment. As will be explained in greater detail below, this transmission is used to correct absorption indicative measurements obtained at the first wavelength to furnish a measurement that is reflective of the actual deposition rate.

Although a Hollow Cathode lamp is utilized in the preferred embodiment of the present invention, it should be evident to one skilled in the art that separate light sources can be used to generate the necessary absorbable and non-absorbable emission lines without departing from the teachings of the present invention.

Turning now to FIG. 1, there is illustrated a vacuum deposition chamber, generally referenced 10, that is of conventional design. A source of material, which is to be deposited upon a substrate 12, is contained within an evaporation boat 11. The boat is situated within the chamber and is connected to an adjustable evaporator power supply 13. As is well known in the art, the evaporator power supply can be regulated to control the rate at which the evaporant material 15 deposits on the substrate.

A Hollow Cathode lamp 17 of the type described is positioned on the left-hand side of the chamber as viewed in FIG. 1. The lamp is arranged to direct a beam of light 18 along a well defined path through the chamber via windows 19 and 20 contained in sidewalls 21 and 22. The windows are constructed of fused silica to freely pass the spectral emission lines of interest without an appreciable loss of energy.

A portion of the output intensity of the lamp is diverted from the main beam 18 by means of a beam splitter 24 along a secondary path of travel 25 onto a photodetector 27 which is an electro-optical transducer capable of converting the intensity of the light incident thereon to a d.c. electrical signal. An optical filter 26 is positioned within the diverted light beam at the optical input to the photodetector. This filter is tuned to selectively pass only the absorbable emission line(s) of the first selected wavelength. Accordingly, the electrical signal from photodetector 27 is indicative of the intensity of the first selected wavelength passing into the optical system. As will be explained below, the output intensity of the first selected wavelength from the light source is monitored continually in order to be able to compensate the measured transmission of this wavelength for any detected changes in the lamp output. Although monitoring the lamp output is useful when the light source output is unstable, this secondary measuring path is not essential for the operation of the invention. For simplicity, the spectral output of the light source will hereinafter be considered stable.

The main beam of light which is passed through the evaporant flow, is directed onto a second photodetector 31 that is similar in construction in the first. An automatic filter changing mechanism 30 is positioned adjacent to the photodetector 31. The mechanism is adapted to selectively position one of the two filters 47,48 within the main beam of light leaving the chamber. Filter 47, which shall herein be referred to as the evaporant line filter, is tuned to pass absorbable emission lines at the first selected wavelength. The second filter 48 contained in the mechanism, which shall herein be referred to as the reference line filter, is tuned to pass non-absorbable emission lines at the second selected wavelength.

Figure 2:
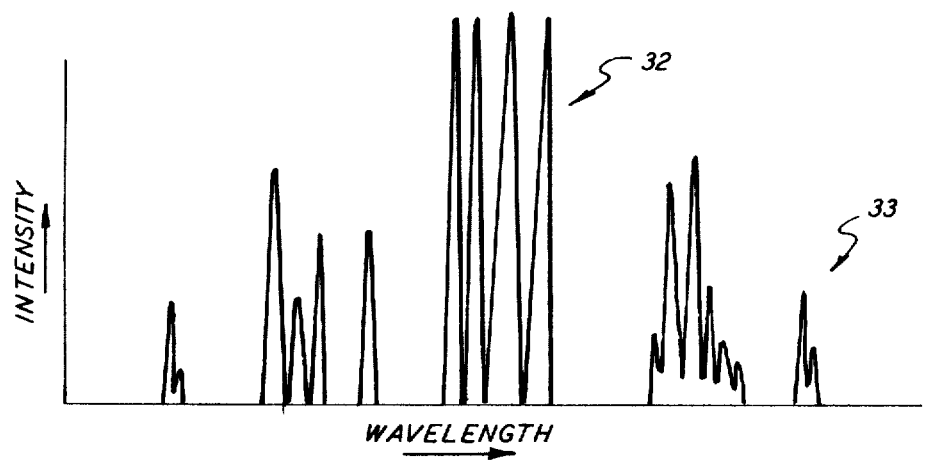
FIG. 2 is a graphic illustration of a typical spectral output from a Hollow Cathode lamp wherein the light intensity is plotted against the wavelength of the radiation.

Although optical filters are described in the preferred embodiment of the invention, any suitable device capable of selectively passing a discrete frequency or band of frequencies while discriminating against other frequencies, as for example, a monochromator, can be used in the practice of the invention. The absorbable emission lines are depicted in FIG. 2 by the curves designated 32 and the non-absorbable emission lines are depicted by the curves designated 33.

With further reference to FIG. 1, the output signals generated by each of the photodetectors 27,31 are coupled to current to voltage amplifiers 37 and 38. The output of these amplifiers is then applied to a pair of synchronously demodulated amplifiers 39 and 40. Amplifiers 39 and 40 are triggered by a frequency generator 35 that is also used to pulse the power supply 36 of the Hollow Cathode lamp. The photodetector signals are synchronously demodulated by these amplifiers so that only a signal modulated at the same frequency as the lamp is passed by the units. In this way the effects of steady state or spontaneous noise signals such as those produced by extraneous light in the system are considerably reduced. Use of a 317 Hz signal from the generator has been found experimentally to minimize noise and is preferred for use in the present system.

As shown in FIG. 1, the output from each synchronously demodulated amplifier is coupled to a pair of analog-to-digital converters 42 and 43 which serve to develop digital signals that are indicative of the amount of energy received by the photodetectors and which are compatible with a general purpose computer 45. The computer may be of any suitable design that is capable of providing the data acquisition and control functions that will be described in detail below. In operation, the computer is programmed to process the light intensity signals furnished by the photodetectors and, in response thereto, generate output signals that are used to control the evaporator power supply 13 and to selectively position filters 47 and 48 in the light path of the optical system. The output signal for controlling the evaporant power supply is provided by means of a digital-to-analog converter 51 while the signals for selecting the appropriate filter are supplied to the filter mechanism 30 by means of digital-to-analog converter 50.

For a better understanding of the data acquisition and control functions required of the computer, the transmission measurements required to obtain the alignment compensated absorption will next be described. As noted earlier, atomic absorption (A) is a function of the deposition rate (R). It is related simply to the alignment compensated transmittance through the evaporant (T) which is also a function of the deposition rate, by:

$$A(R) = 1 - T(R). \tag{1}$$

T, however, can be expressed in terms of the non-alignment compensated transmittance (T') which is a function of not only the deposition rate but also the alignment of the optical elements (S) and the transmittance of the non-absorbing reference emission line or lines ($T_r$) which is only a function of the alignment, whereby:

$$T(R) = \frac{T'(R,S)}{T_r(S)} \tag{2}$$

T'(R,S) and $T_r$(S) represent, respectively, separate ratios of transmission measurements obtained at the first and second selected wavelengths. The term transmission is used here to represent the intensity of an emission line or lines transmitted through the vacuum chamber. Accordingly, T'(R,S) can be further defined as follows:

$$T'(R,S) = \left[\frac{I_m(R,S)}{I_e}\right]_{t=n} \left[\frac{I_e}{I_m(o,S)}\right]_{t=o} \tag{3}$$

where:
$I_m$(R,S) is the intensity of the absorbable emission line or lines after passing through the evaporant flow along a measuring light path;
$I_m$(o,S) is the intensity of the absorbable emission line or lines taken along the measuring light path prior to commensing the evaporant flow;
$I_e$ is the intensity of the absorbable emission line or lines prior to their passing through the evaporant flow;
t = o indicates that the subject measurement is made prior to initiating the evaporant flow; and
t = n indicates that the subject measurment is made after initiating the evaporant flow.

Also, the transmittance of the non-absorbing reference emission line ($T_r$) can be further defined by:

$$T_r(S) = \frac{[I_r]_{t=n}}{[I_r]_{t=o}} \tag{4}$$

where:
$I_r$ is the intensity of the non-absorbable emission line or lines taken at the times indicated.

By combining equations (2)–(4), the alignment compensated transmittance can be expressed in terms of the measured intensities as follows:

$$T(R) = \left[\frac{I_m(R,S)}{I_e}\right]_{t=n} \left[\frac{I_e}{I_m(o,S)}\right]_{t=o} \frac{[I_r]_{t=o}}{[I_r]_{t=n}} \tag{5}$$

The present apparatus utilizes this equation in the computer program to correct measurements of the optical transmittance in two distinct ways. First, random changes in the output intensity of the selected absorbable emission line(s) from the lamp is compensated for. Secondly, changes in transmittance produced by the misalignment of the optical elements are compensated for by measuring the transmission of the non-absorbable emission line or lines. If taken fast enough, these latter measurements provide the potential to compensate the transmittance for interferences which may be caused by moving fixtures crossing the optical path inside the vacuum system.

Figure 3:
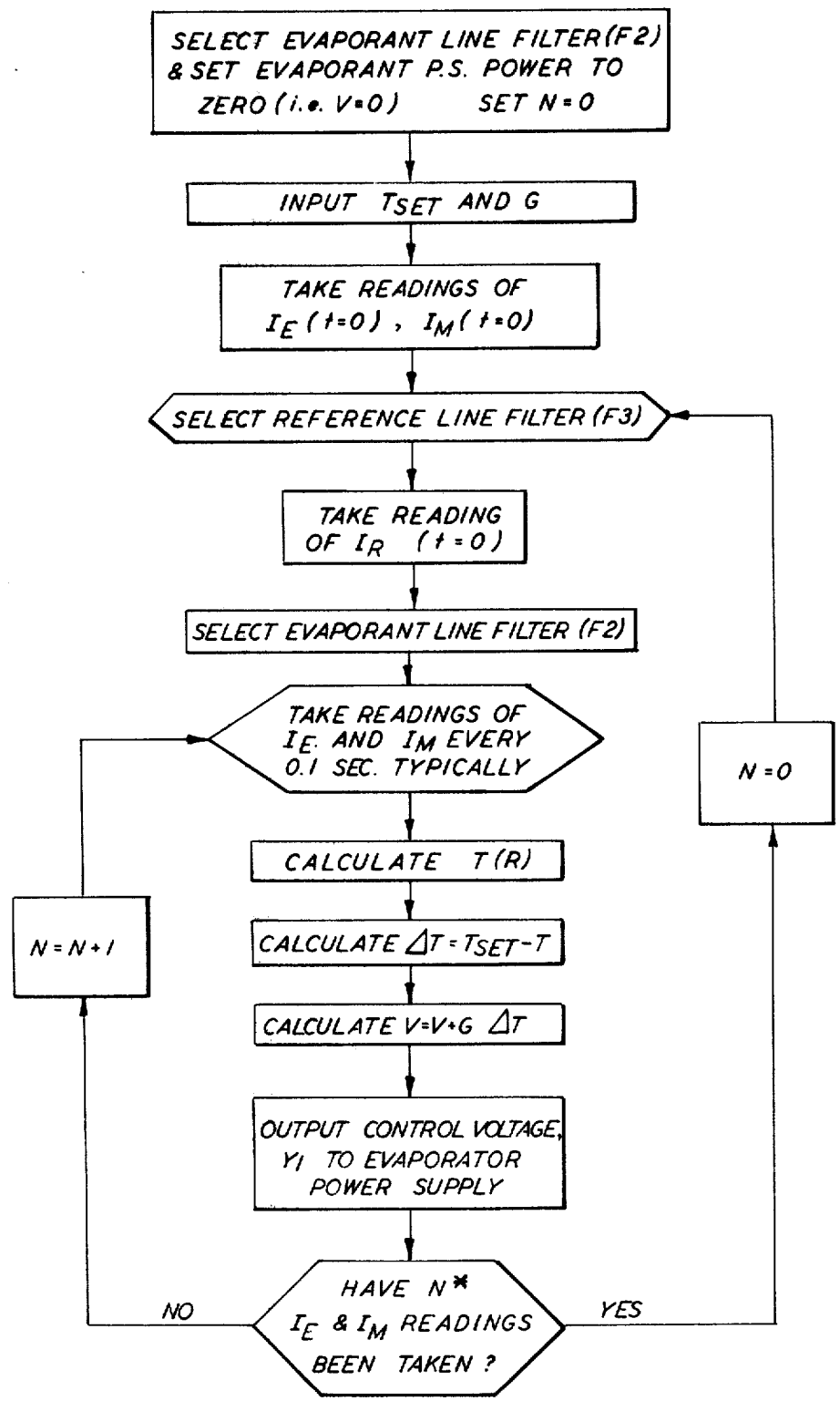
FIG. 3 is a flow diagram of a computer program employed in the monitor/control system shown in FIG. 1.

The operation of the present system shall be described in further detail with reference to the computer flow diagram shown in FIG. 3. At start up, the power output of the evaporant power supply is at zero. The cycle counter (N) is set at zero and the evaporant line filter (F2) is positioned within the main optical path of the system. Predetermined values of the transmittance ($T_{set}$) and gain (G) corresponding to the desired deposition rate and control loop response, respectively, are manually set into the computer.

Prior to initiating the evaporant flow, a zero absorption transmission measurement of the absorbable emission line or lines is taken along with a measurement of the output intensity of this line or lines from the light source ($I_e$) using photo detectors 31 and 27, respectively (FIG. 1). This data is passed on to the computer as noted above.

Following these measurements, the filter mechanism is instructed by the computer to change the position of the two filters whereupon the reference line filter 48 is placed in the main optical path of the system. This filter is arranged to pass only the selected emission line or lines that are not absorbed by the evaporant material. An intensity measurement $(I_r)_{t=o}$ of the second wavelength is then taken under no flow conditions and this information is also passed on to the computer.

The evaporant line filter 47 is again placed in the optical path of the system and power is supplied to the evaporation boat to establish a flow of evaporant within the chamber. As a flow is established, intensity measurements of both $I_e$ and $I_m$ are taken at relatively short intervals. These measurements together with the measurements obtained under no flow conditions are used by the computer to calculate the optical transmittance of the system in accordance with equation (5). This transmittance is compared to the preset transmittance, $T_{set}$. If a difference is detected, the evaporator power supply control signal is adjusted so as to increase or decrease the number density of evaporant atoms to lessen this difference.

Each measuring cycle is counted and the count is continually compared to a preselected number (N*). When coincidence is reached, the filter positions are changed and a new non-absorbable emission line intensity reading, ($I_r$) t=n is taken to replace the value in the computer. The position of the filters is once again changed and an updated series of absorbable emission line(s) transmission measurements taken as explained above. This continual flow of updated information is processed by the computer to maintain the appropriate power supply output.

While this invention has been described with reference to the structure disclosed herein, it is not confined to the details set forth and this application is intended to cover any modifications or changes as may come within the scope of the following claims.

We claim:

1. The method of correcting flow indication measurements in a vacuum deposition system of the type wherein a single atom evaporant is flowed onto a substrate in a vacuum, the steps including
passing radiation containing a first emission line at a wavelength that is absorbable in the single atom evaporant and a second emission line at a wavelength that is not absorbable in said single evaporant through the flow maintained in the chamber along a common optical path, measuring the intensity of the radiation at the first and second emission lines after said radiation has passed through the flow, and correcting the intensity measurement of the first emission line for changes in the intensity of the second emission line to compensate for errors produced by the realignment in the measuring equipment during the measurement period.

2. The method of claim 1 that includes the further step of producing said radiation in a hollow cathode lamp having a cathode containing the single atom evaporant material and an inert fill gas whereby said first and second emission lines are generated from a single source.

3. The method of claim 2 that further includes the steps of monitoring the output of said lamp and correcting the intensity measurements of the first and second emission lines for changes in the output of said lamp.

4. The method of claim 1 that includes the further step of using the corrected intensity measurement of the first emission line to control the rate of evaporation.

5. In a vacuum deposition system wherein a single atom evaporant is flowed onto a substrate in a vacuum apparatus for monitoring said flow that includes source means for directing radiation along an optical path through said single atom evaporant flow, said radiation containing a first emission line at a wavelength that is absorbable by the evaporant and a second emission line at a wavelength that is not absorbable by the evaporant, means for measuring the intensity of the radiation at the first and the second emission line wavelengths after it has passed through the evaporant flow, and means for correcting the measured intensity of the radiation at the first emission line in response for changes in the intensity of the radiation at the second emission line to compensate for errors produced by the realignment of the measuring equipment as the evaporant is being flowed onto the substrate.

6. The apparatus of claim 5 wherein said source means is a hollow cathode lamp having a cathode that is related to the evaporant flow material and a fill gas that is not related to said evaporant material.

7. The apparatus of claim 6 that further includes means to monitor the output intensity of the lamp and to correct both the measured intensities of the first and second emission lines for changes in the output intensity of said lamp.

8. The apparatus of claim 5 that further includes control means that is responsive to the corrected intensity of the first emission line for regulating the amount of flow of evaporant maintained in the vacuum chamber.

* * * * *